(12) United States Patent
Kieftenbeld

(10) Patent No.: US 6,709,836 B2
(45) Date of Patent: Mar. 23, 2004

(54) MOUNTING MEDIUM

(75) Inventor: Wilhelmus Hermanus Hendrikus Maria Kieftenbeld, Raalte (NL)

(73) Assignee: Mallinckrodt Baker B.V., Deventer (NL)

( * ) Notice: Subject to any disclaimer, the term of this patent is extended or adjusted under 35 U.S.C. 154(b) by 161 days.

(21) Appl. No.: 09/968,043

(22) Filed: Oct. 2, 2001

(65) Prior Publication Data

US 2002/0064810 A1 May 30, 2002

(30) Foreign Application Priority Data

Oct. 2, 2000 (EP) .............................. 00203405

(51) Int. Cl.[7] ................................................ G01N 1/30
(52) U.S. Cl. ..................................... 435/40.5; 435/40.5
(58) Field of Search .......................... 435/40.5

(56) References Cited

U.S. PATENT DOCUMENTS 3,498,860 A  3/1970  Pickett

FOREIGN PATENT DOCUMENTS

| GB | 1 201 777 | 8/1970 |
| GB | 2 155 943 A | 10/1985 |
| JP | 58 196220 A | 11/1983 |
| JP | 63 032559 A | 2/1988 |

Primary Examiner—Jean C. Witz
(74) Attorney, Agent, or Firm—Young & Thompson

(57) ABSTRACT

The invention relates to a mounting medium that can be used in the preparation of slides for investigation by microscopy techniques. More in particular the mounting medium comprises a solution, in at least one organic solvent selected from the group consisting of saturated hydrocarbons optionally mixed with one or more alcohols, of at least one (meth)acrylate resin based on one or more monomers having formula I:

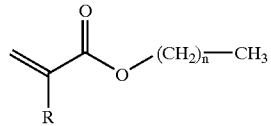

Figure 1:
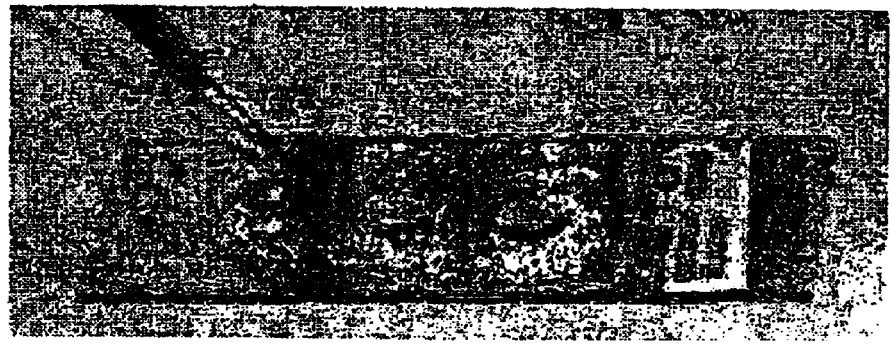

Formula I wherein R is hydrogen or a methyl group and n has a value of 0–19.

The mounting medium of the invention is particularly suited for use in histochemistry, immunochemistry and/or cytochemistry, i.e. to provide slides of samples of blood, cells tissue or other biological fluids or materials, including but not limited to samples/materials which have been stained to facilitate microscopic examination, e.g. for scientific and/or diagnostic purposes.

12 Claims, 1 Drawing Sheet

MOUNTING MEDIUM

The present invention relates to an improved mounting medium that can be used in the preparation of slides for investigation by microscopy techniques.

The mounting medium of the invention is particularly suited for use in histochemistry, immunochemistry and/or cytochemistry, i.e. to provide slides of samples of blood, cells tissue or other biological fluids or materials, including but not limited to samples/material which have been stained to facilitate microscopic examination, e.g. for scientific and/or diagnostic purposes.

Further aspects of the invention will become clear from the description given hereinbelow.

Generally, in microscopy, a slide of a material or sample to be investigated is prepared by putting said sample or material onto a (bottom) slide and then covering said sample with a (top) cover. Generally, for light microscopy or similar techniques, slides and covers of glass or another suitable transparent materials are used.

Also, in the preparation of such slides, the cover glass is usually adhered to/fixated onto the bottom slide. This "mounting" assures that the sample and the cover glass stay in place on the bottom slide, which eases handling, storage and/or transportation of the slides. Also, such mounting assures that the slides are preserved for prolonged periods of time—i.e. for up to five years or more—without substantial deterioration of the sample or material.

Generally, in histochemistry-, cytochemistry-, immunochemistry- or similar medical or biological microscopy techniques, the mounting of the slides is the last step before examination of the specimen by microscope. Thus, in order to provide a better understanding of the present invention, the conventional techniques for the preparation of such slides will now be discussed in more detail, First, one or more samples of the material to be investigated, which may for instance be samples of blood, cells, tissue, or other biological fluids or materials of interest, are put onto the bottom slide. The sample(s) is/are then stained, i.e. to (better) make visible one or more of the components of the sample or material, such as cell nuclei, cell cytoplasm, tissue and cell structures. Such staining techniques and compositions/agents for use therein will be clear to the skilled person, and may for instance include:

stains such as Hematoxylin and eosin (histochemistry),
immunoperoxidase (immunochemistry),
Papanicolaou (cytochemistry) and other histo-, immuno- and cytochemistry stains.

Thereafter, excess staining agent is washed off, e.g. using one or more washing steps with tap and/or distilled/deionized water, alcohol (ethanol, iso-propyl alcohol, benzyl alcohol etc, . . . ) or another suitable medium, Thereafter, the slides are generally washed with an organic solvent or solvent mixture, before the cover glass is fixated onto the bottom slide using the mounting medium. These last washing steps are also intended to remove/replace any water and/or alcohol (ethanol, iso-propyl alcohol, benzyl alcohol etc. . . . ) remaining from the first washing steps with the organic medium, i.e. in order to prepare the sample for the application of the mounting medium. In doing so, the organic solvent acts as an "intermediate" between the water/alcohol and the apolair organic mounting medium.

For instance, the regimen for preparing/mounting a slide may be essentially as described in Table 1

TABLE 1 scheme of mounting a slide (non-limiting):

| Sequence | Time in minutes |
|---|---|
| Staining the specimen on the slide | 1 |
| Aqua dest. | 1 |
| Ethanol 100% | 1 |
| Ethanol 100% | 1 |
| Ethanol 100% | 1 |
| UltraClear/Xylene/Toluene | 1 |
| UltraClear/Xylene/Toluene | 1 |
| UltraClear/Xylene/Toluene | 1 |
| Embedding with mounting medium | |

Conventionally, as indicated in Table 1, xylene or aromatic organic solvents have been used for the last washing steps. However, because the use of such solvents is no longer desired—e.g. for reasons of health and safety—nowadays often (mixtures of) saturated hydrocarbons are used, a commercially available example of which is UltraClear® sold by Mallinokrodt Baker B.V., Deventer, Netherlands, which is a mixture of nonanes, decanes, undecanes and dodecanes.

After washing with the organic solvent (mixture), a few drops of mounting medium is applied to the sample or material, as shown in FIG. 1 (three drops in FIG. 1). Then, the cover glass is applied, which is fixed/adhered (on) to the bottom slide by the mounting medium. Mounting of a coverglass is applied either manually or by a coverslipping machine.

Conventional mounting media usually comprise a resin, such as an acrylate resin, in an aromatic hydrocarbon such as xylene or toluene as organic solvent. However, in practice, it is often found that the conventional mounting media—and in particular the acrylate resin(s) present therein—interfere and/or react with the organic solvent mixture used for washing the slide, resulting in the formation of a turbid layer on the slide and/or leading to other undesired effects which may detract from quality of the slide obtained and/or from the microscopic examination thereof. It has been found that these problems may in particular occur when the last washing step(s) has (have) been carried out with (a mixture of) saturated hydrocarbons, such as UltraClear.

Accordingly, it is an object of the invention to provide an improved mounting medium which can be used in conjunction with organic solvents, such as aromatic hydrocarbons and alcohols—i.e. as used in the preparation of the slides—and in particular with saturated hydrocarbons, without any of the problems indicated above.

It has now been found that such a mounting medium can be provided by the use of an acrylate resin or methacrylate resin as described below.

Thus, in a first aspect, the invention relates to a mounting medium for the preparation of slides, said mounting medium comprising a solution, in at least one organic solvent selected from the group consisting of saturated hydrocarbons optionally mixed with one or more alcohols, of at least one (meth)acrylate resin based on one or more monomers having formula I:

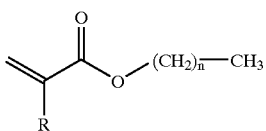

Formula I wherein is hydrogen or a methyl group and n has a value of 0–19.

In particular, the group —(CH$_2$)$_n$—CH$_3$ may comprise a linear "backbone" of between 1 and 10 carbon atoms, which may be substituted at any position(s) with one or more saturated hydrocarbon substituents such as methyl, ethyl, n-propyl, i-propyl, 1-butyl, 2-butyl, i-butyl, etc.; such that the total amount of carbon atoms in the group —(CH$_2$)$_n$—CH$_3$ is between 1 and 20.

Also, and/or alternatively, the group —(CH$_2$)$_n$—CH$_3$ may comprise/contain a saturated hydrocarbon ring and/or an aromatic hydrocarbon ring, which may for instance be connected to the (meth)acrylate group via a (further) saturated hydrocarbon residue, and/or which again may be substituted at any position(s) with one or more saturated hydrocarbon substituents such as methyl, ethyl, n-propyl, i-propyl, 1-butyl, 2-butyl, i-butyl, etc.; again as long as the total amount of carbon atoms in the group —(CH$_2$)$_n$—CH$_3$ is between 1 and 20.

Some particularly preferred examples of the group —(CH$_2$)$_n$—CH$_3$ include, but are not limited to:

methyl
ethyl
iso-propyl;
iso-butyl;
benzyl
iso-hexyl
iso-decyl;

For instance, the (meth) acrylate resin of Formula I may be iso-butyl methacrylate resin, methyl methacrylate, ethyl methacrylate, isopropyl methacrylate, iso-hexyl methacrylate, benzyl methacrylate, iso-decyl methacrylate, as well as the corresponding acrylate resins.

Generally, the mounting medium of the present invention will comprise a solution of one or more of such (meth) acrylate resins in an organic solvent of solvent mixture, such that the amount of (meth)acrylate resins makes up between 10 and 60 wt % of the total composition.

As the organic solvent, any suitable solvent or mixture of solvents may be used, as long as these solvents do not react with the (meth)acrylate resin and/or interfere with the intended action of the mounting medium. Preferably, an aprotic solvent or mixture of aprotic solvents is used, such as a (mixture of) apolair aprotic solvent(s). Some suitable, but non-limiting examples of suitable solvents include:

saturated hydrocarbons, such as linear and/or branched C$_9$–C$_{20}$ (iso)paraffins, in particular C$_8$–C$_{12}$ (iso) paraffins, e.g. nonanes, decanes, undecanes, dodecanes and mixtures thereof; and said saturated hydrocarbons mixed with one or more C$_{1-6}$ alcohols, In one particularly preferred embodiment, the organic solvent or mixture of organic solvents used in (the preparation of) the mounting medium is the same as the organic solvent(s) to be used in the final washing steps of the slide. For instance, in one preferred aspect of the invention, the organic solvent used in the mounting medium is Ultra-Clear®.

The mounting medium of the invention may optionally contain one or more further suitable components such as C$_8$–C$_{12}$ (iso)paraffins.

The mounting medium of the invention may simply be prepared by mixing the (meth)acrylate resin(s) with the organic solvent (mixture) used in the amounts indicated above, and will then usually be ready for use. The mounting medium may also be provided sold as a proprietary/commercial product or formulation, e.g. packaged in a suitable container such as a flask, bottle or dropper bottle, optionally labeled and/or with instructions for use.

Preferably, the mounting medium of the invention is prepared such that it has a final viscosity of between 2 and 6 Stokes—e.g. about 4 Stokes—at 25° C., as measured in a Gardner Bubble viscosimeter. This instrument is based on the principle that the viscosity is directly proportional to the bubble speed.

Also, the mounting medium of the invention is most preferably such that it can be mixed with a saturated hydrocarbon or a mixture of saturated hydrocarbons without resulting in turbidity or other undesired effects. This may be easily ascertained by the skilled person, e.g. by mixing an amount of the mounting medium of the invention with an amount of a saturated hydrocarbon or hydrocarbon mixture (e.g. on a slide or in a vial), followed by visual inspection.

The mounting medium of the invention may be used in a manner known per se and/or essentially analogous to the manner in which conventional mounting media are used, i.e. as described above.

In accordance with the above, the invention provides a mounting medium which is compatible/miscible with alcohols (iso-propyl alcohol, benzyl alcohol), and UltraClear®. Therefore it has a very broad approach.

In addition, the mounting medium of the invention may also provide one or more of the following advantages:

the mounting medium of the invention can be prepared with advantage so as not contain any aromatic compounds and therefore is less hazardous;

the mounting medium has very advantageous flow properties, such as an optimized viscosity (approx. 4 Stokes). This facilitates mounting of the slides;

after mounting of the cover glass, a mounted slide can already be examined within 1 hour and the day after the cover glass is fixed tightly;

after staining the dyes of the staining solutions are bounded to water based cell nucleus and cytoplasm species. In this respect, the mounting medium of the invention is very apolar, when compared to conventional xylene/toluene based mounting media, This means migration of dyes from tissue parts is reduced to a very low extent;

the solvent used in the mounting media of the invention has very low volatility, which doesn't give dry up effects of the slides;

the mounting medium of the invention does not thicken when used. From conventional mounting media, xylene/toluene evaporates and thickens the mounting media when in use;

moistened mounting medium may be easily removed with an organic solvent such as UltraClear®, while some conventional mounting media need to be wiped of thoroughly.

The mounting medium of the invention can be used for all applications known per se for conventional applications, and such uses will be clear to the person skilled in the art, For instance, the mounting medium may be used to prepare slides essentially in the manner outlined above.

As will be clear from the above, the mounting medium of the invention is particularly suited for the preparation of slides in histochemistry, immunochemistry and cytochemistry, e.g. (stained) samples of blood, tissues, cells or other biological materials for examination by light microscopy techniques.

It should however be noted that the invention is not limited to this specific field, not to the preparation of slides for examination by light microscopy. For instance, the mounting medium of the invention may also be used for the preparation of samples for fluorescent microscopy, imaging technology; and/or generally for fixating/preserving (biological) samples on (to) a suitable carrier.

In further aspects, the invention also relates to a method for preparing slides using the mounting medium of the invention, and to the slides obtained via said method.

The invention will now be illustrated by means of the following non-limiting example.

EXAMPLE

A mounting medium was prepared by mixing 25 grams iso-butyl methacrylate resin (sold by Röhm GmbH under the name PLEXIGUM® PQ 611) and 75 ml UltraClear®.

The mounting medium thus obtained was used in the preparation of a slide of a stained sample of blood (cells), essentially according to the steps set out in Table 1 above. The resulting slide was of excellent quality, showing no turbidity or haze. The results are illustrated in FIGS. 2a and 2b, wherein the samples were stained with Hematoxylin/Eosin and coverslipped with the mounting medium (UltraKitt).

Figure 2A:

FIG. 2a: Normal gallbladder has a mucosa with columnar cells lining the branching finger-like projections seen here at high magnification.

Figure 2B:
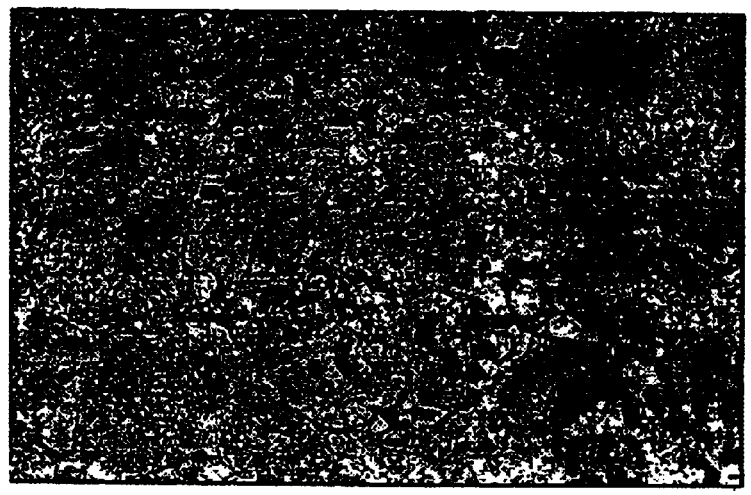

FIG. 2b: The normal glomerulus of the kidney at high power has thin, delicate capillary.

What is claimed is:

1. A method for preparing a slide comprising the steps of:
   a) putting a sample to be investigated onto a bottom slide;
   b) optionally staining said slide;
   c) performing a washing step of said slide with water and/or a protic organic solvent;
   d) performing a washing step of said slide with an aprotic organic solvent or a mixture of aprotic organic solvents;
   e) applying the cover glass with a mounting medium comprising a solution, in at least one saturated hydrocarbon solvent,
   optionally mixed with one or more alcohols, of at least one methacrylate resin having one or more monomers having the following formula:

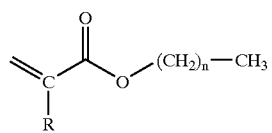

wherein R is hydrogen or a methyl group and n has a value of 0–19.

2. The method according to claim 1, wherein the mounting medium contains, as the one or more organic solvents, the same aprotic organic solvent or the same mixture of aprotic organic solvents as used in step (d).

3. The method according to claim 1, in which the sample is a biological sample.

4. The method according to claim 1, in which the sample has been stained.

5. A slide of a sample to be investigated, obtained by the method of claim 1.

6. The method according to claim 1, in which the group $-(CH_2)_n-CH_3$ comprises a linear backbone of between 1 and 10 carbon atoms, which may be substituted at ay position with one or more saturated hydrocarbon substituents such that the total amount of carbon atoms in the group $-(CH_2)_n-CH_3$ is between 1 and 20.

7. The method according to claim 1, in which the resin of formula is isobutyl methacrylate resin.

8. The method according to claim 1, in which the organic solvent is an aprotic solvent or a mixture of apolar aprotic solvents.

9. The method according to claim 1, in which the solvent is selected from the group consisting of saturated hydrocarbons, or saturated hydrocarbons mixed with one or more $C_{1-6}$ alcohols.

10. The method according to claim 1, in which the organic solvent is Ultraclear® or a similar mixture of saturated iso-paraffins.

11. The method according to claim 1, in which the mounting medium composition comprises between 10 and 60 weight percent of one or more resins based on monomers of the formula and between 40 and 90 weight percent of one or more organic solvents to a total of 100 weight percent of the total composition.

12. The method according to claim 1, in which the mounting medium composition has a viscosity of between 2 and 6 Stokes at 25° C., as measured in a Gardner Bubble viscosimeter.

* * * * *